(12) United States Patent
Kotani

(10) Patent No.: US 12,150,618 B2
(45) Date of Patent: Nov. 26, 2024

(54) CONTROL DEVICE AND FUNCTION RESTRICTION METHOD

(71) Applicant: OLYMPUS CORPORATION, Tokyo (JP)

(72) Inventor: Tadashi Kotani, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 924 days.

(21) Appl. No.: 17/205,413

(22) Filed: Mar. 18, 2021

(65) Prior Publication Data

US 2021/0204795 A1    Jul. 8, 2021

Related U.S. Application Data

(63) Continuation of application No. PCT/JP2019/009984, filed on Mar. 12, 2019.

(30) Foreign Application Priority Data

Sep. 25, 2018 (JP) ................... 2018-179331

(51) Int. Cl.
*A61B 1/00* (2006.01)
*A61B 1/06* (2006.01)

(52) U.S. Cl.
CPC ...... *A61B 1/00013* (2013.01); *A61B 1/00006* (2013.01); *A61B 1/00096* (2013.01);
(Continued)

(58) Field of Classification Search
CPC . A61B 1/00006; A61B 1/00013; A61B 1/0661; A61B 1/00126; A61B 1/0669; A61B 1/0655
See application file for complete search history.

(56) References Cited

U.S. PATENT DOCUMENTS

| 2007/0088193 A1* | 4/2007 | Omori ................ A61B 1/00126 600/101 |
| 2014/0030491 A1 | 1/2014 | Sakai et al. |
| 2017/0172400 A1 | 6/2017 | Shimomura et al. |

FOREIGN PATENT DOCUMENTS

| JP | 3105460 U | 10/2004 |
| JP | 2006015134 A | 1/2006 |
| JP | 2017108932 A | 6/2017 |

OTHER PUBLICATIONS

International Search Report dated May 28, 2019 received in PCT/JP2019/009984.

* cited by examiner

*Primary Examiner* — Aaron B Fairchild
(74) *Attorney, Agent, or Firm* — Scully, Scott, Murphy & Presser, P.C.

(57) ABSTRACT

A control device includes: a light source configured to generate light by drive current applied; a light source controller configured to apply the drive current to the light source; a signal generator configured to generate a signal according to light received; an optical path switch configured to switch an optical path of light generated by the light source; a determination circuit configured to determine whether a signal generated by the signal generator is a periodic signal that periodically changes in signal intensity; and a function controller configured to perform control in which performance of a predetermined function is prohibited when the determination circuit determines that the signal is not the periodic signal and in which the performance of the predetermined function is permitted when the determination circuit determines that the signal is the periodic signal.

11 Claims, 7 Drawing Sheets

(52) U.S. Cl.
CPC ........ *A61B 1/00117* (2013.01); *A61B 1/0655* (2022.02); *A61B 1/0661* (2013.01)

| MODE | LIGHT-SHIELDING MEMBER | |
|---|---|---|
| | YES | NO |
| NORMAL | H | PERIODIC SIGNAL |
| FAILURE IN LIGHT SOURCE | H | H |
| SHORT-CIRCUIT IN SIGNAL GENERATION UNIT | L | L |
| OPENED SIGNAL GENERATION UNIT | H | H |

CONTROL DEVICE AND FUNCTION RESTRICTION METHOD

CROSS REFERENCE TO RELATED APPLICATION

This application is a continuation of PCT international application Ser. No. PCT/JP2019/009984 filed on Mar. 12, 2019 which designates the United States, incorporated herein by reference, and which claims the benefit of priority from Japanese Patent Applications No. 2018-179331, filed on Sep. 25, 2018, incorporated herein by reference.

BACKGROUND

1. Technical Field

The present disclosure relates to a control device and a function restriction method.

2. Related Art

In the related art, endoscope systems have used widely that include an endoscope configured to be inserted into a subject to observe the inside of a subject and a light source device configured to supply laser light for observation to the endoscope has been widely used.

JP 2006-15134 A describes an endoscope system that includes a safety mechanism (interlock) configured to stop supplying laser light from a light source device to an endoscope when the endoscope is disconnected from the light source device. This safety mechanism is a so-called photointerrupter, detecting whether a signal generation unit receive light generated by a light source to detect a connection state between the endoscope and the light source device.

In addition, in a case where the light source device emits laser light, it is necessary to meet safety standards such as JIS C 6802:2014 and IEC 68025-1:2014. Accordingly, it is necessary to consider a single fault condition of the photointerrupter used as the interlock, but a single photointerrupter cannot avoid the loss of safety function due to the single fault or cannot detect the single fault, and thus, it is necessary to provide two or more photointerrupters.

SUMMARY

In some embodiments, a control device includes: a light source configured to generate light by drive current applied; a light source controller configured to apply the drive current to the light source to bring the light source into a state in which the light source repeats on and off at predetermined periodic intervals; a signal generator configured to generate a signal according to light received; an optical path switch configured to switch an optical path of light generated by the light source between a state in which the light path is not incident on the signal generator and a state in which the light path is incident on the signal generator; a determination circuit configured to determine whether a signal generated by the signal generator is a periodic signal that periodically changes in signal intensity, determine that the signal generated by the signal generator is the periodic signal when the signal generated by the signal generator has a signal intensity periodically changed, and determine that the signal generated by the signal generator is not the periodic signal when the signal generated by the signal generator has a constant signal intensity; and a function controller configured to perform control in which performance of a predetermined function is prohibited when the determination circuit determines that the signal is not the periodic signal and in which the performance of the predetermined function is permitted when the determination circuit determines that the signal is the periodic signal.

In some embodiments, a function restriction method includes: applying drive current to a light source to bring the light source into a state in which the light source repeats on and off at predetermined periodic intervals; generating a signal according to light received; determining whether the generated signal is a periodic signal that periodically changes in signal intensity; and performing control in which performance of a predetermined function is prohibited when the generated signal has a constant signal intensity and is determined not to be the periodic signal and in which the performance of the predetermined function is permitted when the generated signal has a signal intensity periodically changed and is determined to be the periodic signal.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
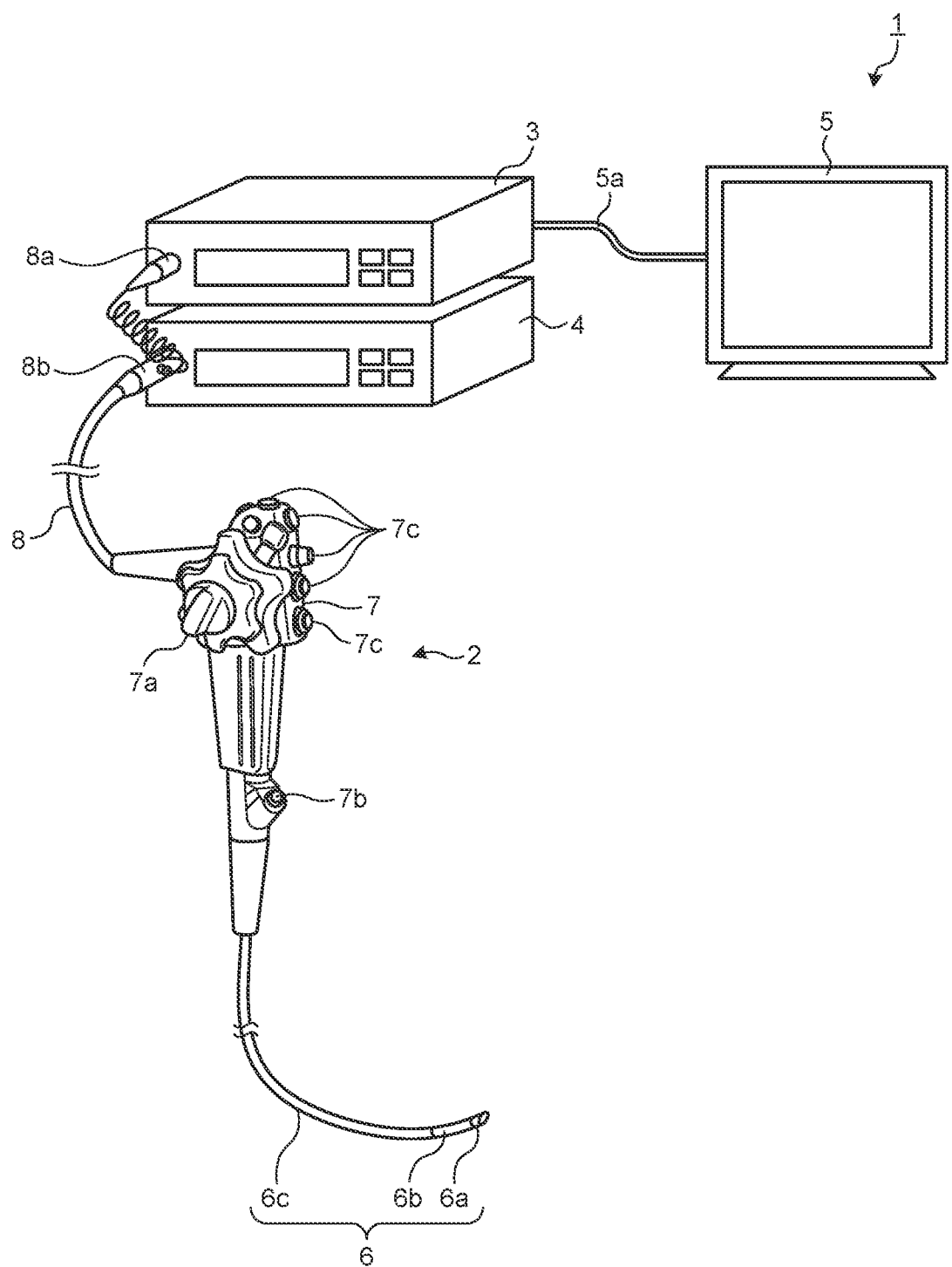
FIG. 1 is a diagram schematically illustrating an overall configuration of an endoscope system as a control device according to an embodiment of the disclosure.

Embodiments of a control device according to the disclosure will be described below with reference to the drawings. Note that the disclosure is not limited to these embodiments.

The disclosure can be generally applied to a control device including a safety mechanism such as a photointerrupter or photoreflector.

Furthermore, in the drawings, the same or corresponding elements are appropriately denoted by the same reference numerals and symbols. In addition, it should be noted that the drawings are schematically illustrated, and dimensional relationships, ratios, and the like between the elements may be different from actual dimensional relationships, ratios, and the like. Some drawings may include portions having different dimensional relationships and ratios between the drawings.

Embodiments

FIG. 1 is a diagram schematically illustrating an overall configuration of an endoscope system as a control device according to an embodiment of the disclosure. As illustrated in FIG. 1, the endoscope system 1 as the control device according to the present embodiment includes an endoscope 2 configured to be inserted into a subject, image inside a body of the subject, and generate an image signal indicating the inside of the subject, an information processing device 3 configured to perform predetermined image processing on the image signal captured by the endoscope 2 and control each unit of the endoscope system 1, a light source device 4 configured to generate illumination light for the endoscope 2, and a display device 5 configured to display an image based on the image signal after the image processing performed by the information processing device 3.

The endoscope 2 includes an insertion portion 6 configured to be inserted into the subject, an operating unit 7 that is positioned on a proximal end side of the insertion portion 6 and is configured to be grasped by an operator, and a flexible universal cord 8 that extends from the operating unit 7.

The insertion portion 6 includes an illumination fiber, an electric cable, an optical fiber, and the like. The insertion portion 6 has a distal end portion 6a that has a built-in imaging unit, a bending portion 6b that includes a plurality of bending pieces and is freely bendable, and a flexible tube portion 6c that is provided on a proximal end side of the bending portion 6b and has flexibility. The distal end portion 6a is provided with a light guide cable configured to illuminate inside the subject through an illumination lens, an observation unit configured to image inside the subject, an opening portion through which a treatment instrument channel passes, and an air/water feeding nozzle.

The operating unit 7 has a bending knob 7a configured to bend the bending portion 6b vertically and horizontally, a treatment instrument insertion portion 7b through which a treatment instrument, such as biopsy forceps or a laser scalpel, is inserted into a body cavity of the subject, and a plurality of switch units 7c configured to operate peripheral devices, such as the information processing device 3, the light source device 4, an air feeding device, a water feeding device, and a gas feeding device. The treatment instrument inserted from the treatment instrument insertion portion 7b is exposed from the opening portion at a distal end of the insertion portion 6, through the treatment instrument channel provided inside the endoscope.

The universal cord 8 includes an illumination fiber, a cable, and the like. The universal cord 8 is branched at a proximal end to have one end being a connector 8a and the other end being a connector 8b. The connector 8a is configured to be attachable to/detachable from a connector of the information processing device 3. The connector 8b is configured to be attachable to/detachable from the light source device 4. The universal cord 8 transmits illumination light emitted from the light source device 4 to the distal end portion 6a, through the connector 8b and the illumination fiber. Furthermore, the universal cord 8 transmits an image signal captured by the imaging unit to the information processing device 3 through the cable and the connector 8a.

The information processing device 3 performs predetermined image processing on an image signal output from the connector 8a and controls the whole endoscope system 1.

The light source device 4 includes a light source configured to emit light for observation, a condenser lens, and the like. Under the control of the information processing device 3, the light source device 4 emits light from the light source and supplies the light, as illumination light for illuminating inside the subject as an object, to the endoscope 2 connected through the connector 8b and the illumination fiber of the universal cord 8.

The display device 5 includes a liquid crystal or organic electro luminescence (EL) display or the like. The display device 5 displays, through a video cable 5a, various information including an image on which the predetermined image processing is performed by the information processing device 3. Thus, the operator is allowed to operate the endoscope 2 while viewing an image (in-vivo image) displayed on the display device 5, for observation of a desired position of the subject and for determination of the characteristics thereof.

Figure 2:
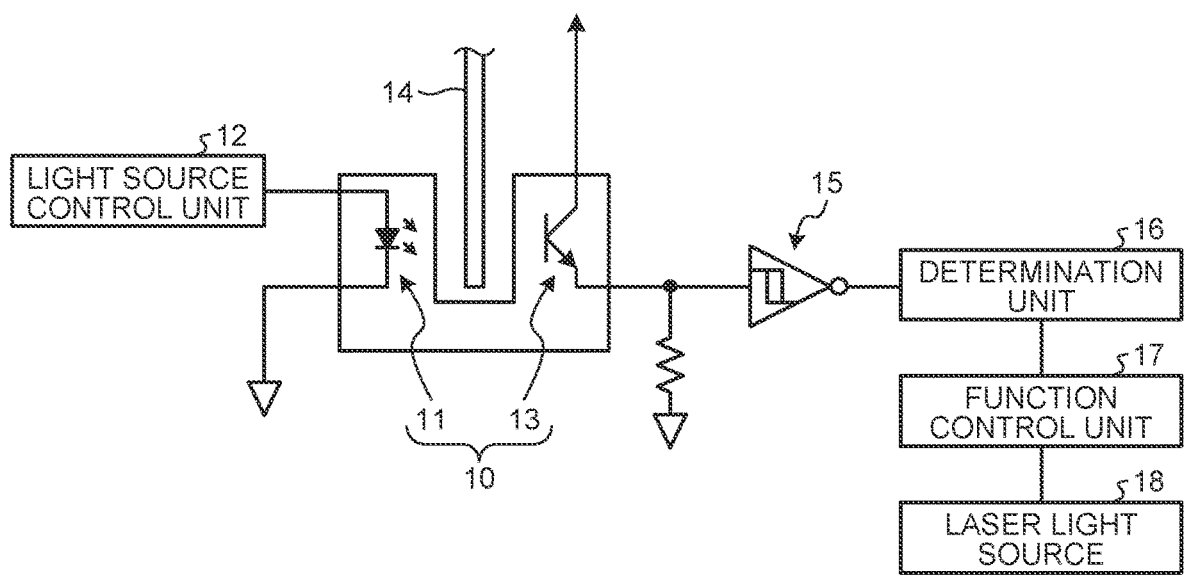
FIG. 2 is a schematic configuration diagram of an interlock mechanism.

FIG. 2 is a schematic configuration diagram of an interlock mechanism. The interlock mechanism illustrated in FIG. 2 is provided, for example, at a portion where the connector 8b of the light source device 4 is connected, and includes a light source 11, a light source control unit 12, a signal generation unit 13, a light-shielding member 14 as an optical path switching unit, a Schmitt trigger 15, a determination unit 16 (determination circuit), a function control unit 17, and a laser light source 18 as an execution unit. The light source control unit 12, the determination unit 16, and the function control unit 17 each are configured by using, for example, a central processing unit (CPU).

The light source 11 generates light by drive current applied. The light source 11 is, for example, a light emitting diode (LED).

Figure 3:
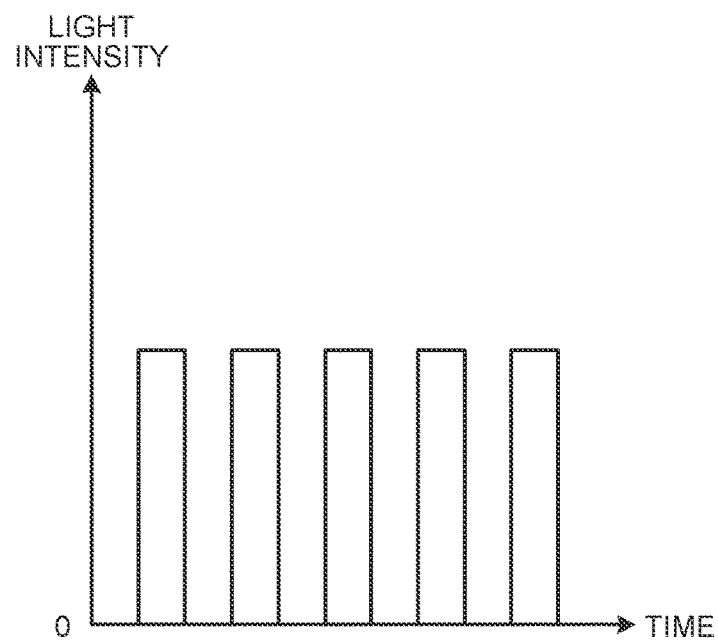
FIG. 3 is a graph illustrating the light intensity of light generated by a light source.

The light source control unit 12 applies drive current to the light source 11 to bring the light source 11 into a state in which the light source 11 repeats on and off at predetermined periodic intervals. FIG. 3 is a graph illustrating the light intensity of light generated by the light source. In FIG. 3, the horizontal axis represents time and the vertical axis represents light intensity. As illustrated in FIG. 3, the light source control unit 12 causes the light source 11 to repeatedly generate a pulse of a predetermined light intensity. Note that the light source control unit 12 causes the light source 11 to repeatedly generate light while the light source device 4 is turned on.

The signal generation unit 13 generates a signal according to light received. The signal generation unit 13 is, for example, a phototransistor. In FIG. 2, the signal generation unit 13 constitutes an emitter follower circuit in which a collector terminal of the phototransistor is connected to a power supply and an emitter terminal is grounded via a resistor.

Note that the light source 11 and the signal generation unit 13 are faced each other and form a photointerrupter 10.

The light-shielding member 14 switches an optical path of light generated by the light source 11 between a state in which the light path is not incident on the signal generation unit 13 and a state in which the light path is incident on the signal generation unit 13. Specifically, the optical path of light is switched between a state in which the light-shielding member 14 is inserted between the light source 11 and the signal generation unit 13 so as to block incidence of light generated by the light source 11 on the signal generation unit 13 and a state in which the light-shielding member 14 is removed from between the light source 11 and the signal generation unit 13 so as to make light generated by the light source 11 incident on the signal generation unit 13.

The Schmitt trigger 15 removes a fluctuation (noise) in signal generated by the signal generation unit 13 and outputs the signal as a digital signal to the determination unit 16. Here, an inverting buffer IC is used, and when the phototransistor of the signal generation unit 13 is on, that is, when the signal generation unit 13 detects light from the light source 11, the output of the signal generation unit 13 has a voltage that is substantially equal to power supply voltage, and the output of the Schmitt trigger 15 shows an L level. Meanwhile, when the phototransistor of the signal generation unit 13 is off, that is, when the signal generation unit 13 detects no light from the light source 11, the output of the signal generation unit 13 becomes the ground level, and the output of the Schmitt trigger 15 shows an H level.

The determination unit 16 determines whether a signal generated by the signal generation unit 13 is a periodic signal that periodically changes in signal intensity. Specifically, the determination unit 16 determines whether an output signal from the Schmitt trigger 15 is the periodic signal that changes periodically. However, the determination unit 16 may directly determine whether a signal generated by the signal generation unit 13 is the periodic signal that changes periodically in signal intensity, without interposing the Schmitt trigger 15. Furthermore, when an output signal from the Schmitt trigger has a constant level, the determination unit 16 determines that the signal is not the periodic signal. The function control unit 17 controls the laser light source 18 to have a prohibition state in which performance of a predetermined function is prohibited when the determination unit 16 determines that a signal is not the periodic signal, and controls the laser light source 18 to have a permission state in which the performance of the predetermined function is permitted when the determination unit 16 determines that a signal is the periodic signal. Specifically, when the determination unit 16 determines that the signal is not the periodic signal, the function control unit 17 brings the laser light source 18 into the prohibition state in which the supply of laser light to the endoscope 2 is prohibited. Meanwhile, when the determination unit 16 determines that the signal is the periodic signal, the function control unit 17 brings the laser light source 18 into the permission state in which the supply of laser light to the endoscope 2 is permitted.

As the predetermined function, the laser light source 18 generates laser light supplied to the endoscope 2.

Figure 4:
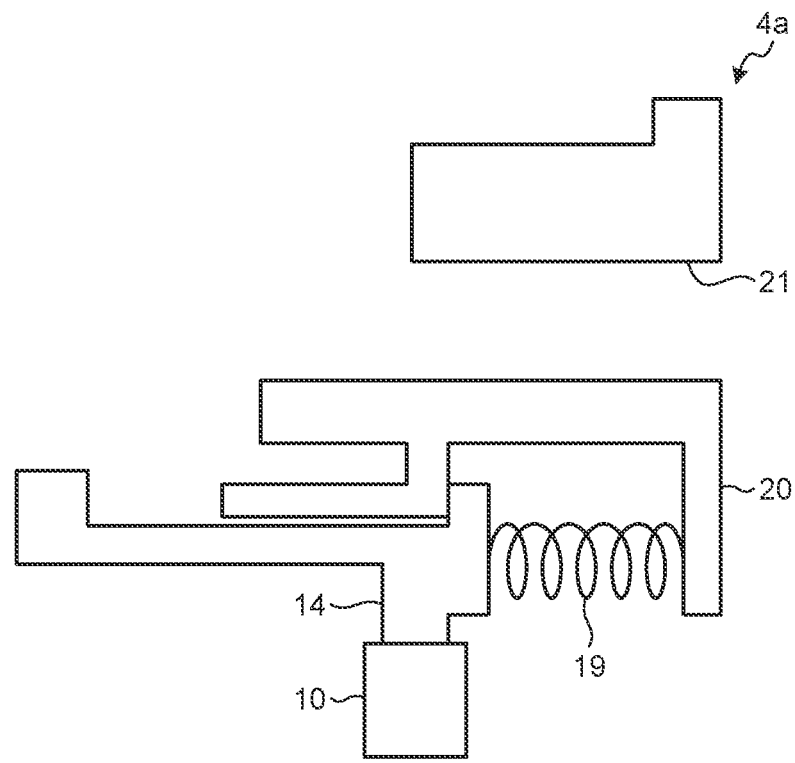
FIG. 4 is a diagram illustrating a state in which no endoscope is connected to a light source device illustrated in FIG. 1.

Next, connection states between the endoscope 2 and the light source device 4 will be described. First, a state in which the endoscope 2 is not connected to the light source device 4 will be described. FIG. 4 is a diagram illustrating a state in which no endoscope is connected to the light source device illustrated in FIG. 1. As illustrated in FIG. 4, a connector 4a of the light source device 4 includes a spring 19, a holding portion 20, and a hole portion 21. The connector 4a is configured to connect the endoscope 2.

Figure 5:
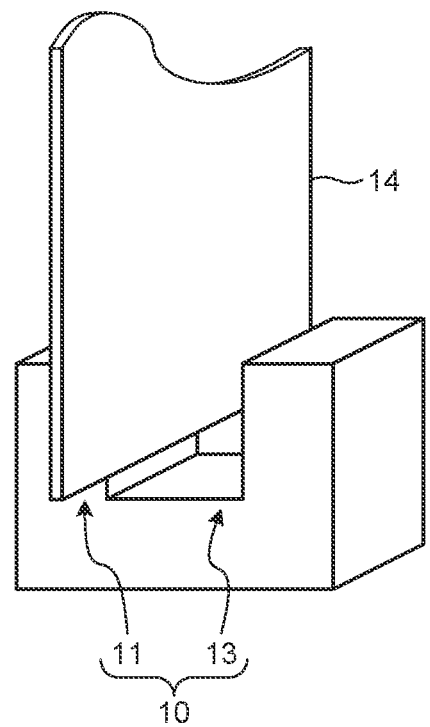
FIG. 5 is an enlarged perspective view of a photointerrupter and a light-shielding member illustrated in FIG. 4.

FIG. 5 is an enlarged perspective view of the photointerrupter and the light-shielding member illustrated in FIG. 4. As illustrated in FIG. 5, the spring 19 urges the light-shielding member 14, and while the endoscope 2 is not connected to the light source device 4, the light-shielding member 14 is inserted between the light source 11 and the signal generation unit 13.

The holding portion 20 holds the spring 19 and positions the light-shielding member 14 that is urged by the spring 19.

The connector 8b is fitted into the hole portion 21.

Figure 6:
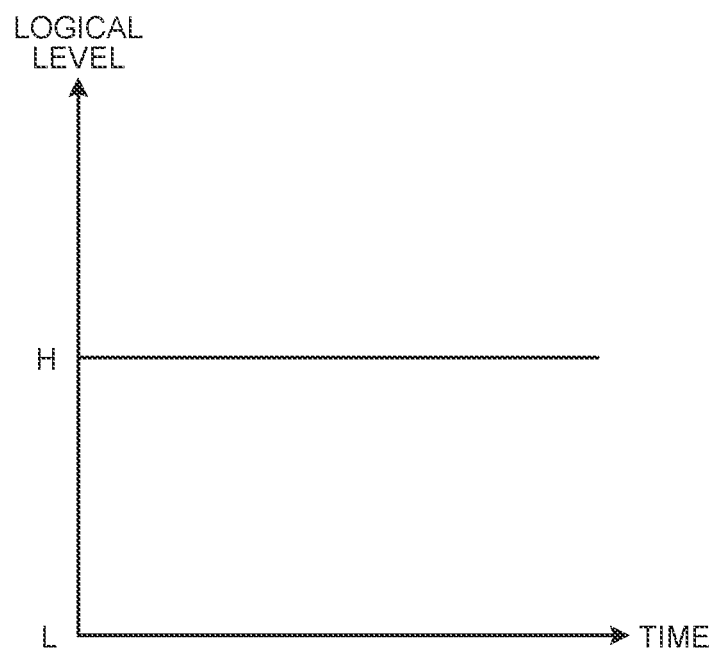
FIG. 6 is a diagram illustrating the logical level of a signal output by a Schmitt trigger in a case where no endoscope is connected to the light source device.

FIG. 6 is a diagram illustrating the logical level of a signal output by the Schmitt trigger in a case where no endoscope is connected to the light source device 4. In FIG. 6, the horizontal axis represents time and the vertical axis represents signal intensity. As illustrated in FIG. 6, when the endoscope 2 is not connected to the light source device 4, light generated by the light source 11 is shielded by the light-shielding member 14 and is not incident on the signal generation unit 13, and thereby the phototransistor of the signal generation unit 13 is off, and an output from the Schmitt trigger 15 has a constant H level.

At this time, the determination unit 16 determines that the signal generated by the signal generation unit 13 is not the periodic signal. Therefore, the function control unit 17 brings the laser light source 18 into the prohibition state in which the supply of laser light to the endoscope 2 is prohibited. In other words, when the endoscope 2 is not connected to the light source device 4, the laser light source 18 is in the prohibition state in which the supply of laser light to the endoscope 2 is prohibited, ensuring safety.

Figure 7:
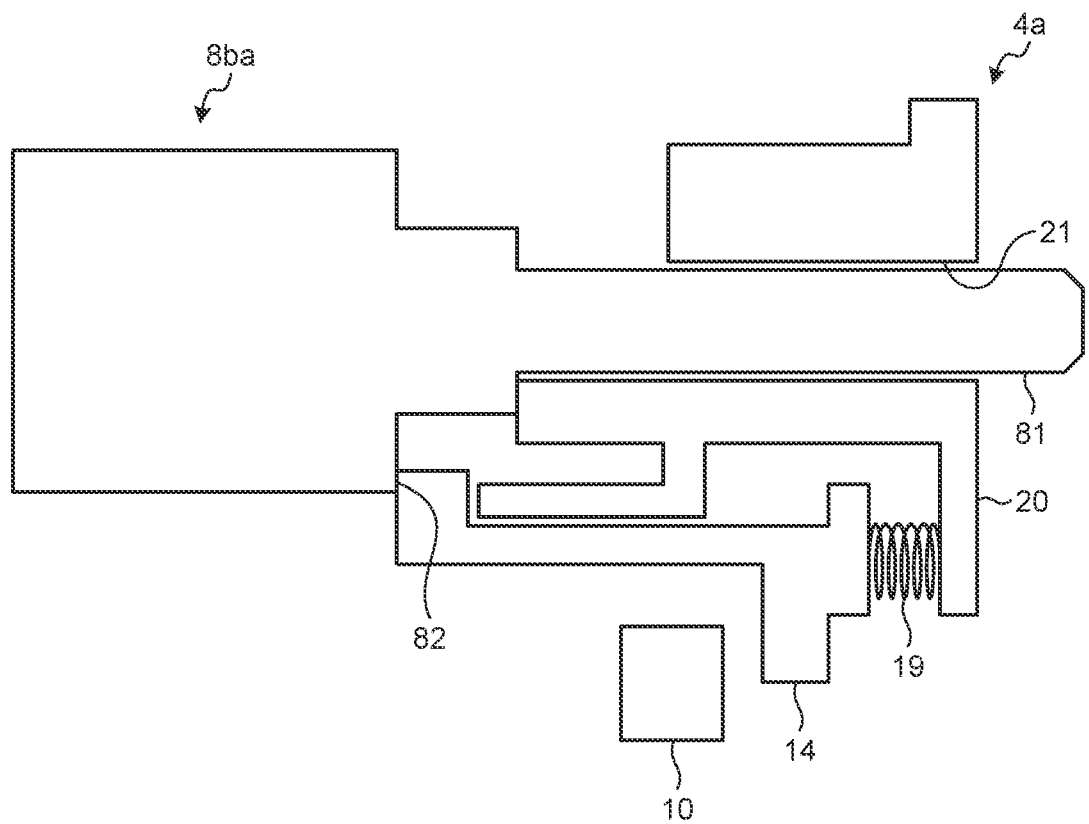
FIG. 7 is a diagram illustrating a state in which an endoscope is connected to the light source device illustrated in FIG. 1.

Next, a state in which the endoscope 2 is connected to the light source device 4 will be described. FIG. 7 is a diagram illustrating a state in which the endoscope is connected to the light source device illustrated in FIG. 1. As illustrated in FIG. 7, when the endoscope 2 is connected to the light source device 4, an inserted portion 81 of a connector 8ba is inserted into the hole portion 21 of the light source device 4. At this time, an abutment portion 82 of the connector 8ba abuts on the light-shielding member 14, and the light-shielding member 14 is removed from between the light source 11 and the signal generation unit 13.

Figure 8:
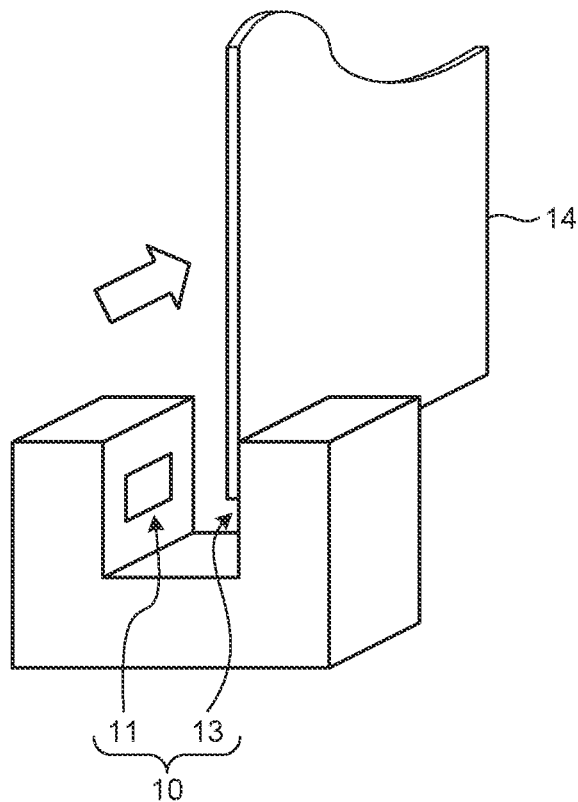
FIG. 8 is an enlarged perspective view of the photointerrupter and the light-shielding member illustrated in FIG. 7.

FIG. 8 is an enlarged perspective view of the photointerrupter and the light-shielding member illustrated in FIG. 7. As illustrated in FIG. 8, when the endoscope 2 is connected to the light source device 4, the light-shielding member 14 is removed from between the light source 11 and the signal generation unit 13, and light generated by the light source 11 is incident on the signal generation unit 13.

Figure 9:
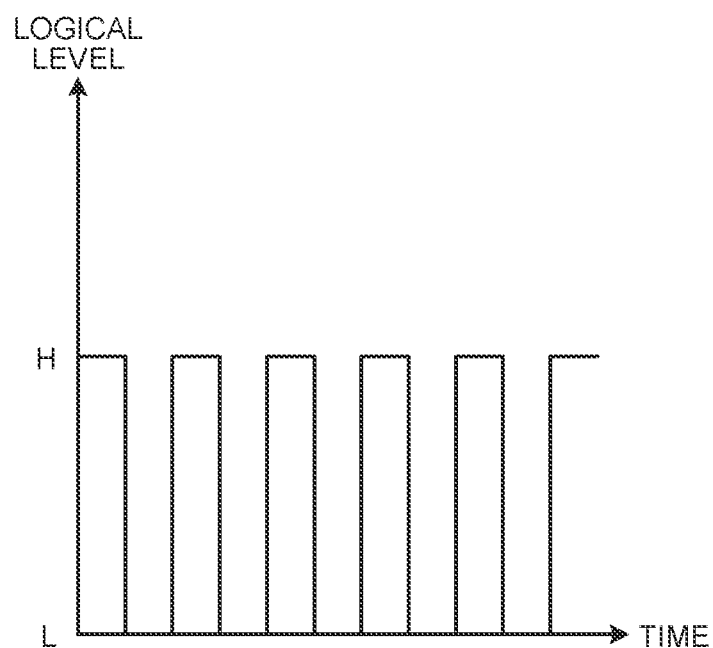
FIG. 9 is a graph illustrating the logical level of a signal output by the Schmitt trigger in a case where the endoscope is connected to the light source device.

FIG. 9 is a graph illustrating the logical level of a signal output by the Schmitt trigger in a case where the endoscope is connected to the light source device. As in FIG. 6, the horizontal axis represents time and the vertical axis represents signal intensity, in FIG. 9. As illustrated in FIG. 9, when the endoscope 2 is connected to the light source device 4, light generated by the light source 11 is not shielded by the light-shielding member 14 and is incident on the signal generation unit 13, and thereby the signal generation unit 13 receives the light generated by the light source 11 and generates a signal. Therefore, the signal generated by the signal generation unit 13 has the same period as the light generated by the light source 11, the signal intensity changes periodically between the substantially power supply voltage and the ground level, and the output of the Schmitt trigger 15 changes periodically between the L level and the H level.

At this time, the determination unit 16 determines that the signal generated by the signal generation unit 13 is the periodic signal. Therefore, the function control unit 17 brings the laser light source 18 into the permission state in which the supply of laser light to the endoscope 2 is permitted. In other words, when the endoscope 2 is connected to the light source device 4, the laser light source 18 is in the permission state in which the supply of laser light to the endoscope 2 is permitted.

Figures 10, 11:
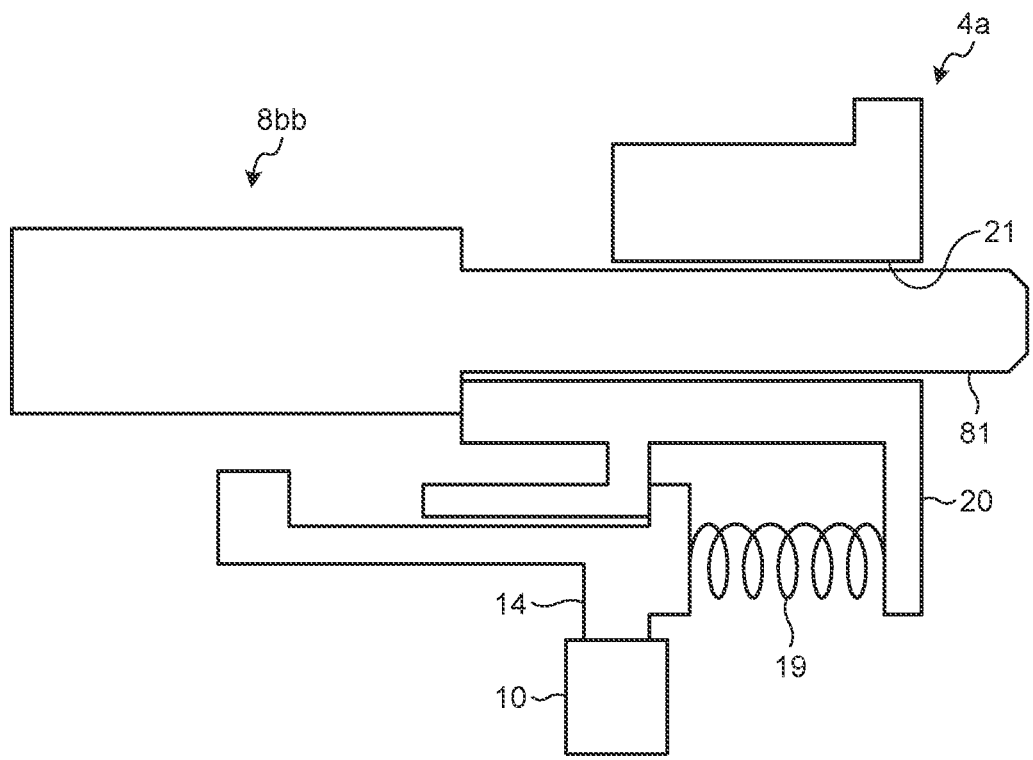
FIG. 10 is a diagram illustrating a state in which an endoscope not compatible with a laser light source is connected to the light source device illustrated in FIG. 1.
FIG. 11 is a table illustrating signals output by the Schmitt trigger.

Next, a state in which an endoscope 2 that is not compatible with the laser light source 18 is connected to the light source device 4 will be described. FIG. 10 is a diagram illustrating a state in which the endoscope not compatible with the laser light source is connected to the light source device illustrated in FIG. 1. As illustrated in FIG. 10, when the endoscope 2 not compatible with the laser light source 18 is connected to the light source device 4, the inserted portion 81 of a connector 8bb is inserted into the hole portion 21 of the light source device 4. Meanwhile, the connector 8bb includes no abutment portion, and thereby the position of the light-shielding member 14 is maintained. Therefore, the light-shielding member 14 remains being inserted between the light source 11 and the signal generation unit 13. Therefore, a signal generated by the signal generation unit 13 is the same as the signal illustrated in FIG. 6.

At this time, the determination unit 16 determines that the signal generated by the signal generation unit 13 is not the periodic signal. Therefore, the function control unit 17 brings the laser light source 18 into the prohibition state in which the supply of laser light to the endoscope 2 is prohibited. In other words, when the endoscope 2 not compatible with the laser light source 18 is connected to the light source device 4, the laser light source 18 is in the prohibition state in which the supply of laser light to the endoscope 2 is prohibited, ensuring safety.

Next, a case of failure in the light source 11 or the signal generation unit 13 will be described. In the case of failure in the light source 11, the light source 11 does not generate light, and thereby a signal generated by the signal generation unit 13 shows a constant value as illustrated in FIG. 6. In this case, the determination unit 16 determines that the signal generated by the signal generation unit 13 is not the periodic signal. Therefore, the function control unit 17 brings the laser light source 18 into the prohibition state in which the supply of laser light to the endoscope 2 is prohibited.

In a case where the signal generation unit 13 is short-circuited, the signal has a voltage equal to the power supply voltage of the phototransistor, and an output from the Schmitt trigger 15 shows the L level. Meanwhile, in a case where the signal generation unit 13 is opened, the Schmitt trigger 15 shows the H level, as illustrated in FIG. 6. In either case, the determination unit 16 determines that the signal generated by the signal generation unit 13 is not the periodic signal. Therefore, the function control unit 17 brings the laser light source 18 into the prohibition state in which the supply of laser light to the endoscope 2 is prohibited.

In other words, when either the light source 11 or the signal generation unit 13 has a failure, the laser light source 18 is in the prohibition state in which the supply of laser light to the endoscope 2 is prohibited, ensuring safety.

The contents described above are illustrated in FIG. 11. FIG. 11 is a table illustrating signals output by the Schmitt trigger. As illustrated in FIG. 11, according to the endoscope system 1, only when the light source 11 and the signal generation unit 13 operate normally and further the endoscope 2 compatible with the laser light source 18 is connected to the light source device 4, the signal generation unit 13 detects the periodic signal, and the laser light source 18 is in the permission state in which the supply of laser light to the endoscope 2 is permitted. Therefore, the endoscope system 1 is a control device that is configured to ensure safety by using a single safety device.

Modifications

In the embodiments, examples using the photointerrupter 10 have been described, but the disclosure is not limited to these examples. For example, a photoreflector may be used.

Figure 12:
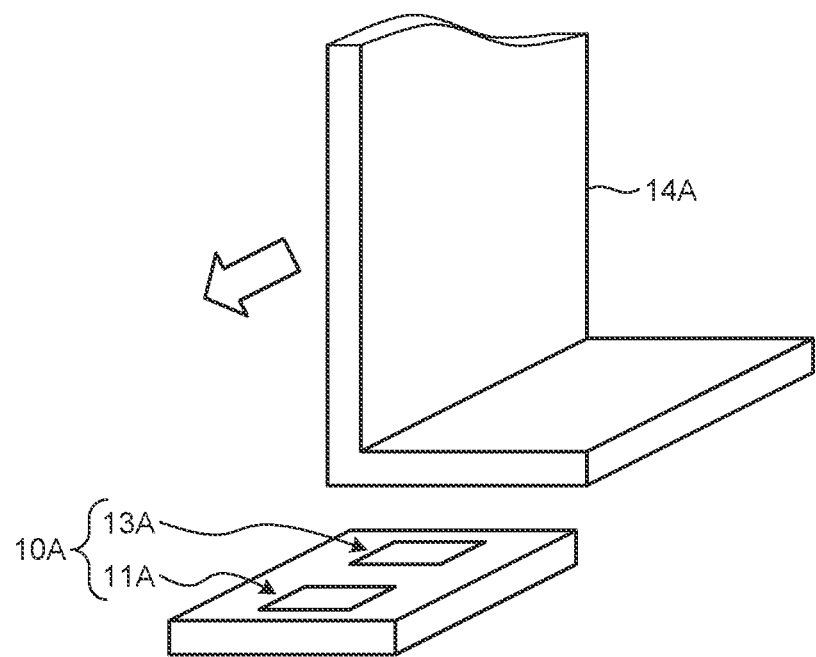
FIG. 12 is a perspective view of a photoreflector and a reflection member according to a modification.
Figure 13:
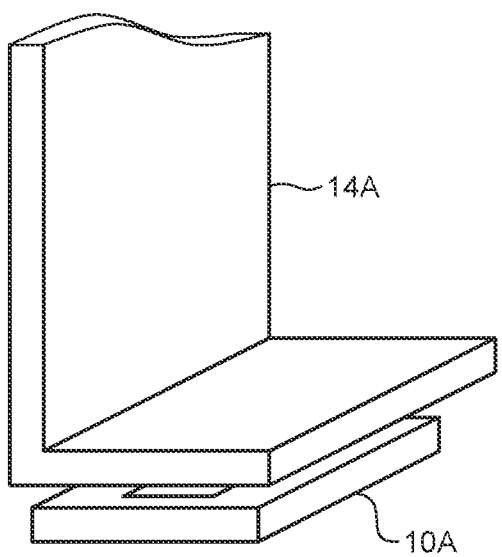
FIG. 13 is a perspective view of the photoreflector and the reflection member according to the modification.

FIGS. 12 and 13 are perspective views of a photoreflector and a reflection member according to a modification. As illustrated in FIGS. 12 and 13, a light source 11A and a signal generation unit 13A are aligned on the same surface and form a photoreflector 10A.

The optical path of light is switched between a state in which a reflection member 14A as the optical path switching unit is removed from the optical path of light generated by the light source 11A so as to block incidence of light generated by the light source 11A on the signal generation unit 13A and a state in which the reflection member 14A is inserted into the optical path of light generated by the light source 11A so as to reflect the light generated by the light source 11A and make the light incident on the signal generation unit 13A.

The endoscope system 1 may be configured by using the photoreflector 10A described above, instead of the photointerrupter 10. Furthermore, the safety mechanism is not limited to the photointerrupter 10 and the photoreflector 10A and may have a configuration in which a reflection member is inserted and removed between the light source and the signal generation unit to switch between a state in which light generated by the light source is incident on the signal generation unit and a state in which the light is not incident thereon. Furthermore, the inclination of a reflection member inserted between a light source and a signal generation unit may be changed relative to an optical path so as to be switched between a state in which light generated by the light source is incident on the signal generation unit and a state in which the light is not incident thereon.

Note that in the embodiments described above, the configuration in which components of the light source 11 to the function control unit 17 are arranged in the light source device 4 has been described, but the disclosure is not limited to this configuration. For example, any one of the components may be arranged in the endoscope.

Furthermore, the embodiments described above uses, but is not limited to, the control device according to the disclosure, for the connection between the endoscope 2 and the light source device 4. For example, the control device according to the disclosure can be used for an opening/closing device for a door opening/closing portion or the like, a connector between a video device and a projector, and the like.

According to the disclosure, it is possible to achieve the control device that is configured to ensure safety by using a single safety device.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. A control device comprising:
   a light source configured to generate light by an applied drive current;
   a light source controller comprising hardware, the light source controller configured to apply the drive current to the light source to bring the light source into a state in which the light source repeats on and off at predetermined periodic intervals;

a signal generator configured to:
  receive light generated by the light source; and
  generate a signal according to the received light;
an optical path switch configured to switch an optical path of light generated by the light source between a state in which the light path is not incident on the signal generator and a state in which the light path is incident on the signal generator;
a determination circuit configured to:
  determine whether a signal generated by the signal generator is a periodic signal that periodically changes in signal intensity,
  determine that the signal generated by the signal generator is the periodic signal when the signal generated by the signal generator has a signal intensity periodically changed, and
  determine that the signal generated by the signal generator is not the periodic signal when the signal generated by the signal generator has a constant signal intensity; and
a function controller comprising hardware, the function controller configured to perform control in which performance of a predetermined function is prohibited when the determination circuit determines that the signal is not the periodic signal and in which the performance of the predetermined function is permitted when the determination circuit determines that the signal is the periodic signal.

2. The control device according to claim 1, wherein
the light source and the signal generator face each other, and
the optical path switch is configured to switch an optical path of light between a state in which the optical path switch is inserted between the light source and the signal generator so as to block incidence of light generated by the light source on the signal generator and a state in which the optical path switch is removed from between the light source and the signal generator so as to make light generated by the light source incident on the signal generator.

3. The control device according to claim 1, wherein
the optical path switch is configured to switch an optical path of light between a state in which the optical path switch is removed from an optical path of light generated by the light source so as to block incidence of the light generated by the light source on the signal generator and a state in which the optical path switch is inserted into an optical path of light generated by the light source so as to reflect the light generated by the light source and make the reflected light incident on the signal generator.

4. The control device according to claim 1, wherein the light source comprises a first light source and the light comprises first light, and the control device further comprising:
  a connector configured to connect an endoscope; and
  a second light source configured to generate second light supplied to the endoscope as the predetermined function,
wherein the optical path switch is configured to bring:
  the first light generated by the first light source into a state in which the first light generated by the first light source is not incident on the signal generator when no endoscope is connected to the connector, and
  the first light generated by the first light source into a state in which the first light generated by the first light source is incident on the signal generator when the endoscope is connected to the connector, and
the function controller is configured to:
  cause the second light source to bring into a prohibition state in which supply of second light to the endoscope is prohibited when the determination circuit determines that the signal generated by the signal generator is not the periodic signal, and
  cause the second light source to bring into a permission state in which the supply of second light to the endoscope is permitted when the determination circuit determines that the signal is the periodic signal.

5. The control device according to claim 4, the second light source comprises a laser light source configured to generate laser light supplied to the endoscope as the predetermined function.

6. The control device according to claim 1, wherein when the signal generator is short-circuited, the signal generator is configured to output a non-periodic signal as the signal.

7. The control device according to claim 1, wherein when the signal generator is opened, the signal generator is configured to output a non-periodic signal as the signal.

8. The control device according to claim 1, wherein the optical path switch comprises an obstruction and a photosensor, the obstruction is provided between the light source and the sensor, the obstruction configured to be movable between:
  a first position obstructing the light from the light source; and
  a second position not obstructing the light from the light source.

9. The control device according to claim 8, wherein the function controller is configured to:
  prohibit—a second light source from outputting a—second light when the obstruction is at a first position,
  permit the second light-source to output the second light when the obstruction is at the first position.

10. The control device according to claim 1, wherein the first signal is a digital signal indicated only as one of a high level signal or a low level signal.

11. The control device according to claim 10, wherein the sensor is configured to:
  generate the high level signal when the sensor receives light from the light source, and
  generate the low level signal when the sensor doesn't receive light from the light source.

* * * * *